(12) United States Patent
Singh et al.

(10) Patent No.: US 11,284,850 B2
(45) Date of Patent: Mar. 29, 2022

(54) REDUCED INTERACTION CT SCANNING

(71) Applicant: Siemens Healthcare GmbH, Erlangen (DE)

(72) Inventors: Vivek Singh, Princeton, NJ (US); Ankur Kapoor, Plainsboro, NJ (US); Philipp Hölzer, Baltimore, MD (US); Bogdan Georgescu, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 74 days.

(21) Appl. No.: 16/817,824

(22) Filed: Mar. 13, 2020

(65) Prior Publication Data

US 2021/0282730 A1    Sep. 16, 2021

(51) Int. Cl.
| | |
|---|---|
| *A61B 6/00* | (2006.01) |
| *A61B 6/03* | (2006.01) |
| *G06T 7/00* | (2017.01) |
| *G06T 15/08* | (2011.01) |
| *G06T 11/00* | (2006.01) |

(52) U.S. Cl.
CPC .............. *A61B 6/488* (2013.01); *A61B 6/032* (2013.01); *A61B 6/466* (2013.01); *A61B 6/481* (2013.01); *A61B 6/5205* (2013.01); *G06T 7/0012* (2013.01); *G06T 11/005* (2013.01); *G06T 15/08* (2013.01); *G06T 2207/10081* (2013.01); *G06T 2207/20081* (2013.01); *G06T 2207/20084* (2013.01); *G06T 2207/30204* (2013.01)

(58) Field of Classification Search
CPC ........ G16H 30/40; G16H 50/20; A61B 34/10; A61B 2034/55; A61B 6/488; A61B 6/032; A61B 6/466; A61B 6/481; A61B 6/5205; G06T 7/0012; G06T 11/005; G06T 15/08; G06T 2207/10081; G06T 2207/20081; G06T 2207/20084; G06T 2207/30204
See application file for complete search history.

(56) References Cited

U.S. PATENT DOCUMENTS

| | | |
|---|---|---|
| 9,524,582 B2 | 12/2016 | Ma |
| 10,475,538 B2 | 11/2019 | Wu |
| 2018/0033049 A1 | 2/2018 | Mayfield |
| 2018/0228450 A1* | 8/2018 | Vega ..................... A61B 6/032 |
| 2019/0005751 A1 | 1/2019 | Warren |
| 2019/0005752 A1 | 1/2019 | Dyne |
| 2019/0021677 A1* | 1/2019 | Grbic .................. A61B 5/7292 |
| 2019/0031849 A1 | 1/2019 | Nakanishi |
| 2019/0034726 A1 | 1/2019 | Shriver |
| 2019/0320994 A1* | 10/2019 | Lemaitre ................. G01T 7/005 |

(Continued)

OTHER PUBLICATIONS

U.S. Appl. No. 16/283,864, filed Feb. 25, 2019.

(Continued)

*Primary Examiner* — Vu Le
*Assistant Examiner* — Julius Chai (57) ABSTRACT

Systems and methods for a reduced interaction CT scanning workflow. A sensor is used to capture an image of a patient on the table. Scan parameters are automatically set. A full CT scan is performed without a scout scan. During the full CT scan, the scan parameters are adjusted based on the raw CT measurements from the full CT scan. A radiology report is automatically generated from the results of the full CT scan.

17 Claims, 6 Drawing Sheets

(56) References Cited

U.S. PATENT DOCUMENTS

2021/0144074 A1\* 5/2021 Guaneri ................ A61B 34/25
2021/0183055 A1\* 6/2021 Rao ...................... G06T 7/0012

OTHER PUBLICATIONS

U.S. Appl. No. 16/592,924, filed Oct. 4, 2019.
"FAST Integrated Workflow." Siemens Healthineers, https://www.siemenshealthineers.com/en-us/computed-tomography/technologies-innovations/fast-integratedworkflow. Accessed on Mar. 12, 2020.

\* cited by examiner

REDUCED INTERACTION CT SCANNING

FIELD

The present embodiments relate to medical therapy or imaging.

BACKGROUND

In existing computer tomography (CT) scanners, an operator helps a patient onto the scanning table and operates the CT scanner. A scout scan is performed of the patient. The scout scan generates a preliminary image used to make sure the region of interest is included in the field of view of the full scan, to check the exposure technique, and/or as a baseline prior to administration of contrast material. After the scout scan is performed, the operator sets the scanning parameters as dictated or verified by the scout scan and performs the full scan. The generated image is then looked at by a radiologist who analyzes the image and creates a radiology report based on the observed findings. The entire workflow can take several minutes or longer depending on the complexity of the scan. In time-critical settings such as that of trauma, this forces the physician or the surgeon in a difficult position where the physician or surgeon has to make a decision whether to first get a scout scan, full scan, and report before looking at the patient or to use that invaluable time to directly begin the procedure. Without a scan, however, the surgeon would not have any prior imaging to plan the procedure and would have to risk making observations only during the procedure.

In addition, different patients differ significantly in size, height, and weight, which can make manual positioning by the operator difficult and time-consuming. And, operators themselves have different body heights, which can impact table height and vantage points. In many cases, the patient is not located at an isocenter of the CT scanner, which leads to increased dose, affects image quality, and can potentially lead to rescans.

SUMMARY

Systems, methods, and computer readable media are provided for a reduced interaction CT scanning workflow. A full CT scan is performed without first performing a scout scan by estimating scan parameters from surface data of a patient acquired by a sensor. During the full CT scan, the scan parameters are adjusted as a function of the raw CT data from the scan. A radiology report is automatically generated from the results of the CT scan.

In a first aspect, a method is provided for reduced interaction medical imaging. The method includes capturing, with a camera, surface data representing a patient; registering, by a processor, the surface data to a model of the patient; estimating, by the processor, scan parameters for a CT scanner from the registered image data; initiating a scan by the CT scanner with the scan parameters without performing a scout scan; adjusting, during the scan, the scan parameters as a function of acquired scan data during the scan; and outputting a radiology report after completing the scan.

In one embodiment, the scan parameters are estimated using a network trained using machine training.

In one embodiment, the scan parameters comprise at least one of a start slice position, an end slice position, an expected absorption curve, or dose. The start slice position and the end slice position may correspond to anatomical landmarks identified on the registered surface data.

In one embodiment, estimating the scan parameters comprises: estimating a three-dimensional model of the patient; and using markers on the three-dimensional model and a selected protocol to estimate the scan parameters.

In one embodiment, wherein the scan parameters are estimated by registering a prior CT scan of the patient to the surface data and using the prior CT scan to estimate the scan parameters.

In one embodiment, the adjustment of scan parameters using machine training comprises comparing the predicted scan parameters with current measurements from the CT scanner as the scan is being generated and setting the scan parameters based on the comparison. An end slice position of the scan parameters may be adjusted as a function of current measurements indicating an unexpected change in density values in raw data from the CT scanner.

In one embodiment, one or more uncertainty measures are calculated during registration of the surface data to the model of the patient; wherein the one or more uncertainty measures are propagated through the estimating and adjusting of the scan parameters.

In one embodiment, the method further comprises stopping the scan when an estimate for the scan parameters with the one or more uncertainty measures are outside a range of errors.

In one embodiment, the radiology report is generated using a machine trained network trained to process one or more regions of interest and classify any pathologies present.

In a second aspect, a medical system for reduced interaction CT scanning without preforming a scout scan includes a sensor, a Ct scanner, and a processor. The sensor is configured to capture surface data of a patient. The CT scanner is configured to scan the patient using one or more scan parameters and generate CT scan data. The processor is configured to estimate the one or more scan parameters using machine training, initialize the CT scanner with the estimated one or more scan parameters, and adjust the one or more scan parameters during a scan of the patient by the CT scanner as a function of received CT scan data.

In one embodiment, the processor is further configured to automatically generate a radiology report from an output of the CT scanner.

In one embodiment, the system further includes a display configured to display the radiology report.

In a third aspect, a method is provided for reduced interaction medical imaging. The method includes capturing, with a three-dimensional camera, surface data representing an outer surface of a patient; generating a synthetic topogram from the surface data; generating, by dose modulation software, one or more scan parameters from the synthetic topogram without performing a scout scan; initiating a scan by a CT scanner with the one or more scan parameters; adjusting, during the scan, the one or more scan parameters as a function of acquired scan data during the scan; and outputting a radiology report after completing the scan.

In one embodiment, the synthetic topogram includes uncertainty measures calculated as a function of a range of possible error values during generation.

In one embodiment, estimating the scan parameters with uncertainty estimates comprises using a machine trained network trained to obtain a generalized probability distribution of the scan parameters.

In one embodiment, adjusting the scan comprises: adjusting the scan parameters constrained by the range of error values.

In one embodiment, the method further includes registering the surface data to a patient model as a function of a prior scan. The synthetic topogram is generated from the registered surface data.

In one embodiment, outputting the radiology report includes generating the radiology report using a machine trained model trained to classify one or more pathologies in a CT image.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION

Embodiments provide a CT scanning workflow where a sensor is used to capture an image of a patient on the table. Scan parameters are automatically set. The full CT scan is performed without a scout scan. During the full CT scan, the scan parameters are adjusted based on the raw CT measurements from the full CT scan. A radiology report is then automatically generated from the results of the full CT scan.

Embodiments significantly boost the scanning workflow efficiency. In certain time-critical settings including trauma or emergency settings, a scout scan may not need to be used as a larger tolerance to scan parameter estimates may be allowed if it can significantly speed up the scanning workflow. Such a speed up might be the difference between whether a surgeon requests a scan, especially in trauma settings, or decides to go without any prior imaging (due to the additional time that it takes to perform a scout scan and configure the scanner). In addition to saving time, by skipping the scout scan, the patient may receive less radiation dose and may be more comfortable due to less time on the table. Further, automation of the scanning workflow limits user or operator errors due to poor training or misunderstandings.

In certain embodiments, the initial setting of the scanning parameters and adjustments may be within a margin of error for the scanning system. However, outliers in patient types may result in poor outcomes. In an embodiment, an uncertainty measure may be associated with each step of the workflow. The uncertainty measure represents a possible range of errors in the calculations. The uncertainty measure may be subsequently propagated through the entire workflow. The uncertainty measure may be used as a confidence measure, for example, of whether the scans and results are sufficiently usable (which may not be the case in unexpected scenarios) and may also be used as a threshold to determine if the operator should step in, stop the scan and perform a manual procedure.

Figure 1:
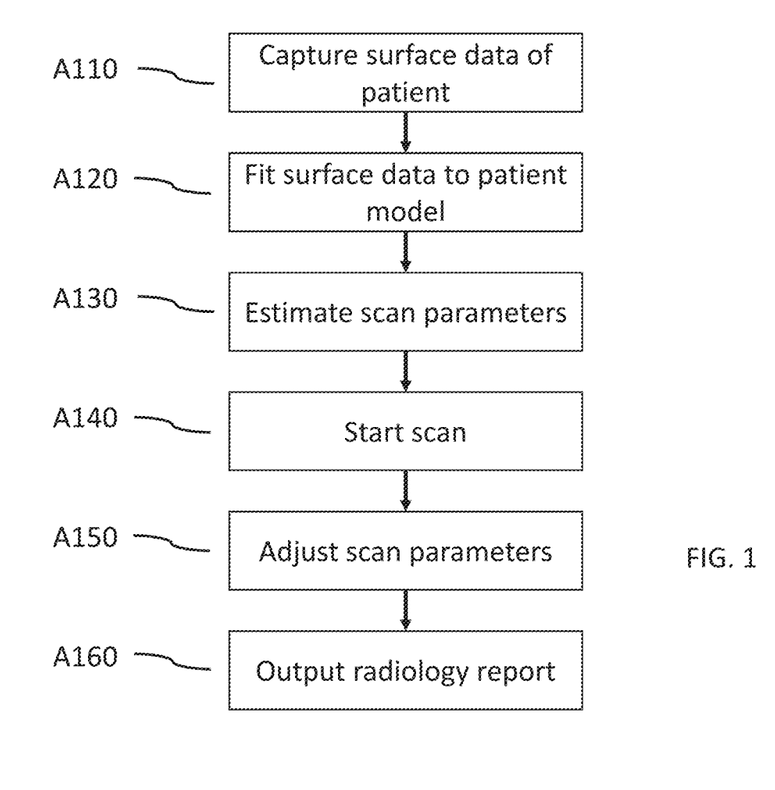
FIG. 1 depicts a flow chart diagram of one embodiment of a method for reduced interaction scanning.
Figure 6:
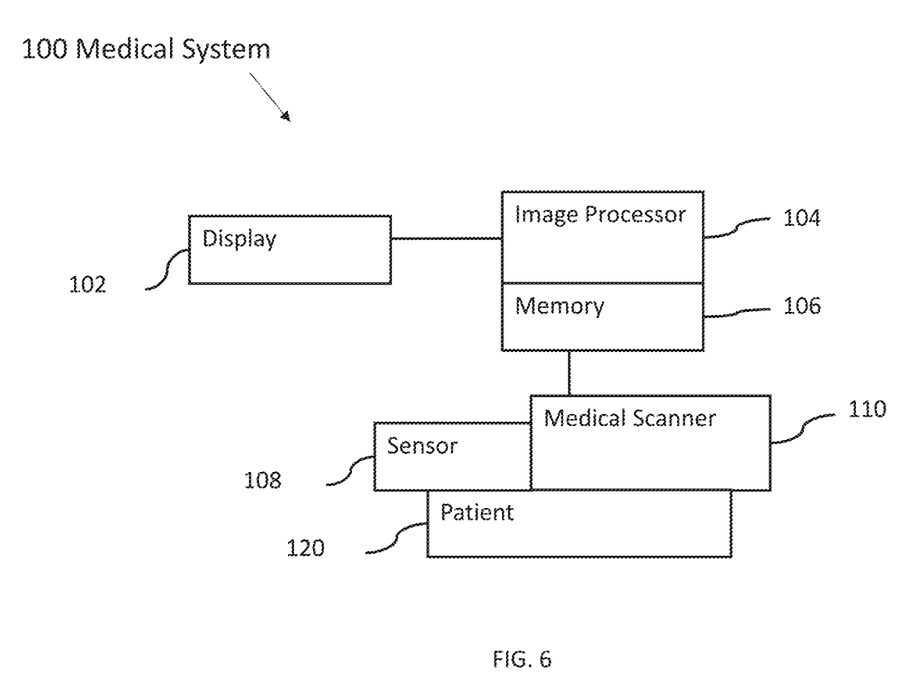
FIG. 6 depicts a system for reduced interaction scanning according to an embodiment.

FIG. 1 is a flow chart diagram of one embodiment of a method for reduced interaction CT imaging. The method of FIG. 1 is performed by a medical system 100, such as the medical system 100 of FIG. 6. FIG. 6 depicts one embodiment of a medical system 100 for reduced interaction medical imaging. The medical system 100 of FIG. 6 includes the display 102, memory 106, image processor 104, sensor 108, and medical scanner 110. A patient 120 is depicted as being prepared to be or being scanned by the medical scanner 110. The medical system 100 may be a medical imaging system (e.g., CT scanner, magnetic resonance (MR) scanner, positron emission tomography (PET) scanner, single photon emission computed tomography (SPECT) scanner, ultrasound scanner, x-ray scanner, or other diagnostic imaging scanner 110) and/or a medical therapy system (e.g., x-ray therapy system). The sensor is provided to capture data of the patient surface. The image processor 104 determines scan parameters based on the output of the camera 108 and configures and controls the medical system 100. Other devices may be used to perform any of the acts.

The method of FIG. 1 is performed in the order shown (e.g., top to bottom or numerical), but other orders may be used. Act A150 may be repeated over the length of a scan. Additional, different or fewer acts may be provided. For example, act A120 may not be used or may be altered if there is prior scan data.

The method of FIG. 1 is performed without requiring a preliminary or scout image or film of the patient. A preliminary or scout image is normally taken of a body region before a definitive imaging study—e.g., a scout scan before a CT scan. "Scouts" serve to establish a baseline and may be used before performing angiography, CT, or MRI. A scout scan or film is a preliminary image obtained prior to performing the major portion of a particular study. There may be one or more reasons to get a scout scan: to make sure the region of interest is included in the field of view, to check the exposure technique, or as a baseline prior to administration of contrast material. In the case of a typical CT study, the scout scan is used to plot the locations where the subsequent slice images will be obtained. The scout scan may also be typically used as input for dose modulation software. The proposed workflow obviates the need for a scout scan and thus results in a significant boost in efficiency.

Figure 2A:
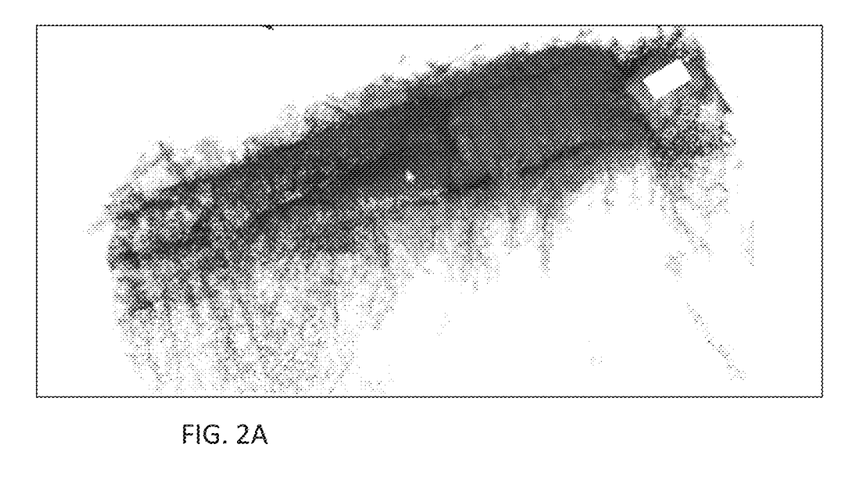
FIGS. 2A and 2B respectfully depict an example of surface data acquired by a sensor and a fit model based on the surface data.

At act A110, a sensor captures an outer surface of a patient. The sensor is directed at a patient. The sensor captures the outer surface of the patient from one or more perspectives. Any portion of the outer surface may be captured, such as the entire patient viewed from one side from head to toe and hand to hand or just the torso. The sensor captures the outer surface with the patient in a particular position, such as capturing a front facing surface as the patient lies in a bed or on a table for treatment or imaging. FIG. 2A depicts surface data of a patient acquired from a depth sensor.

The outer surface is the skin of the patient. In other embodiments, the outer surface includes clothing. The sensor may use a frequency that passes through clothing and detects skin surface. Alternatively, the outer surface is the clothing and the fitting of the patient model accounts for the clothing.

The outer surface is captured as depths from the sensor to different locations on the patient, an image or photograph of the outside of the patient, or both. The sensor outputs the sensed image and/or depths. The measurements of the outer surface from the sensor are surface data for the patient. FIG. 2 shows an example image from surface data where the intensity in grayscale is mapped to the sensed depth. Alternatively, the sensor measurements are processed to determine the outer surface information, such as stereoscopically determining the outer surface from camera images from different angles with image processing.

In one embodiment, the surface data may include different representations of the patient. Two or more channels are created. For example, two images have pixel intensity modulated by the amplitude of the information for the channel (e.g., one by depth and the other by color). In one embodiment, given a three-dimensional surface of the patient's body (skin surface), two-dimensional projections of the data—skin surface image (e.g., height of the surface from the scanner table at each location in the image) and depth image (e.g., measure the thickness of the person at each location in the image)—are formed by image processing from the output of the sensor. Each channel provides different information. One channel provides a distance or height of front surface locations to a bed or table on which the patient lies, to the sensor, and/or relative to another location. The outer surface as sensed and the known location of the sensor to the bed are used to determine the distance. Another channel is a thickness of the patient. The thickness may be a difference of a given depth from the maximum and minimum depth. Other thickness may be used. The first channel stores the depth of the body surface as observed from the front or looking at the patient resting on the patient bed, and second channel stores the thickness computed by measuring the distance between the closest and furthest point as observed from the front. Other channels may be used, such as one channel for depth from the sensor and another channel for optical image of the patient. Other surface data may be used.

The surface data is used at the resolution of the sensor. For example, the surface data is at 256×256 pixels. Other sizes may be used, including rectangular fields of view. The surface data may be filtered and/or processed. For example, the surface data is altered to a given resolution. As another example, the surface data is down sampled, such as reducing 256×256 to 64×64 pixels. Each pixel may represent any area, such as each pixel as down sampled to 64×64 representing 1 cm$^2$ or greater. Alternatively, the sensor captures at this lower resolution. The surface data may be cropped, such as limiting the field of view. Both cropping and down sampling may be used together, such as to create 64×64 channel data from 256×312 or other input channel data. Greater or lower resolution may assist in regression. In another approach, the surface data is normalized prior to input. The surface data is rescaled, resized, warped, or shifted (e.g., interpolation). The surface data may be filtered, such as low pass filtered.

The camera 108 may capture surface data from before the patient is placed on the bed, such as starting to capture upon power-up, triggered by the user, or triggered by an appointment in a schedule. In an embodiment, a stream of data is captured over time. Since a stream is captured, a sequence of frames of surface data representing the bed without and with the patient is acquired. Once the patient is placed or starts to lay upon the bed, the surface data reflects the patient on the bed. The table (bed) occupancy detection stage detects if the table is occupied by the patient and accordingly notifies to system to proceed to a body detection stage. The detection of the patient may or may not continue once the patient is detected.

Figure 2B:
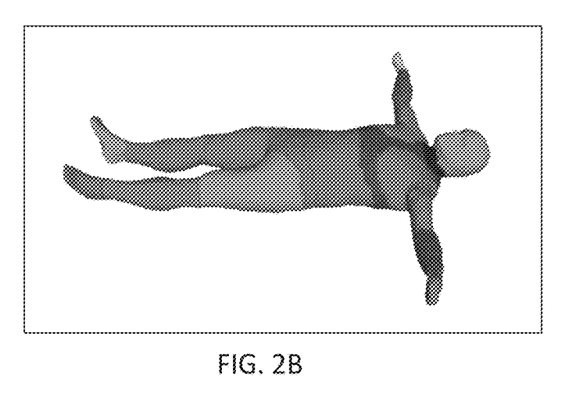

At act A120, the processor 104 fits a patient model to the surface data. The patient model is a generic representation of surface of a human or part of a human. FIG. 2B depicts a fit model of the patient. Different models may be used for different body types, such as a male or female model. The patient model is not specific to the patient. For example, the patient model is a statistical shape model. The patient model is not specific to any other patient or is specific to a patient meeting a norm. Any representation may be used for the model. In one embodiment, the model is formed from a mesh, such as a mesh of triangles. Other meshes may be used. Other representations of a three-dimensional surface may be used.

Any now known or later developed fit of a body surface model to captured surface data for a patient may be used. For example, a SCAPE model is fit to the surface data based on minimization of differences. In one embodiment, the depth camera image of a subject is converted to a three-dimensional point cloud. A plurality of anatomical landmarks is detected in the three-dimensional point cloud. A three-dimensional avatar mesh is initialized by aligning a template mesh to the three-dimensional point cloud based on the detected anatomical landmarks. A personalized three-dimensional avatar mesh of the subject is generated by optimizing the three-dimensional avatar mesh using a trained parametric deformable model (PDM). The optimization is subject to constraints that consider clothing worn by the subject and the presence of a table on which the subject in lying.

In an embodiment, a statistical shape model is fit to the depths as the surface data. The statistical shape model is a mesh or other representation of an average or other statistical representation of an outside of a human or part of a human. The statistical shape model includes probabilities or other constraints on alteration, so that the fitting maintains the shape based on statistics.

In another embodiment, a personalized three-dimensional mesh of a person is generated by a model-based approach to fit a human skeleton model to depth image data of the person. The estimated pose skeleton is then used to initialize a detailed parametrized deformable mesh (PDM) that was trained in an offline training phase. The PDM is then optimized to fit the input depth data by perturbing the body pose and shape. A sampling-based optimization procedure fits the PDM to the depth data. Unlike the shape completion and animation of people (SCAPE) model, which is only applied to data with a skin clad subject, the sampling-based approach deals with clothing variations of the subject. Furthermore, the sampling-based approach also enables embodiments to deal with bias introduced due to sensor noise.

At act A130, the processor 104 estimates scan parameters using machine training. The registered patient model and/or surface data may be used as inputs. The scan parameters may include start and end slice positions, detector configuration, tube current, tube potential, reconstruction algorithm, patient positioning, scan range, reconstructed slice thickness, pitch, among others. The medical system 100 and scan parameters are configured, at least in part, based on the patient model as fit to the patient. The image processor 104 or a controller of the medical system 100 sets one or more values of programmable variables for imaging or treating the patient. The medical scanner 110 may configure itself. The image processor 104 may directly configure the medical scanner 110. The configured medical system 100 and medical scanner 110 may then treat or image the patient using the determined scan parameter values.

The scan parameters may be determined using a machine trained model/network that inputs the fit patient model and outputs one or more scan parameters. A fully connected neural network, convolutional neural network, or another neural network may be used. A support vector machine, clustering based machine training, Bayesian, or other machine trained model may be used. For training the machine trained model, the machine trained model arrangement or architecture is defined. The definition is by configuration or programming of the training. The number of layers or units, type of training/learning, and other characteristics of the network are controlled by the programmer or user. In other embodiments, one or more aspects (e.g., number of nodes, number of layers or units, or type of training) are defined and selected by the machine during the training. Training data, including many samples of frames of surface data and the corresponding ground truth (i.e., accurate or verified scan parameters), is used to train the model. The relationship of the input surface data to the output scan parameters is machine trained. Once trained, the machine trained model may be applied to the CT scanning workflow after acquisition of the surface data and generation of the fit patient model. Training and application may be used for any of the machine trained models for generating scan parameters, fitting the patient model, generating the surface data, or adjusting the scan parameters during the scan. Different machine trained models are configured, trained using different training data, and applied for different purposes.

The fit patient model of act A120 may indicate the locations of start and end points for a range of scanning along a torso of the patient. Based on the reason for the scan (e.g., region to diagnose and/or to treat), the fit patient model may be used to configure parameters that control the movement of the gantry or range of scanning. The intensity used (e.g., dose) may be set, such as based on a size of the patient determined from the fit model. The patient model as fit may define a field of view and/or x-ray intensity to control dose or scan range. The fit model may be useful for positioning the scanner and controlling the x-ray source. Any setting or parameter of the medical scanner 110 may be determined or configured based on the fit model or a value (e.g., estimated weight or height) derived from the fit model. The pose, scan range and/or iso-center of the scan range may be based on the fit model.

In an embodiment, the scan parameters may be estimated using a process that estimates a three-dimensional model of the patient and uses markers on the model to determine the scan range based on selected protocol. The process may also provide the correct isocenter position, enabling the right dose modulation and consistent images, support scanning the correct body region with no truncation by aligning the automatically identified anatomical position with the protocol and may help safeguard the right scan direction, which may be crucial when moving the table with infused patients. In an embodiment, the scan parameters may be directly regressed as the start and end slice positions may correspond to estimated anatomical landmarks.

In an embodiment, the scan parameters may be estimated by registering a prior CT scan of the patient to the sensor data and using the prior scan to estimate the scan parameters. In trauma situations, for example, multiple scans may be performed over a period of time to check on the status of a patient. The prior scans may be used as an input for fitting the surface data to a patient model and/or setting the scan parameters. For example, if a prior scan has been performed, the system may be able to more accurately predict the location of internal organs or objects based on the prior scan data.

In an embodiment, the scan parameters may include an uncertainty measure. The uncertainty measure corresponds to a level or range of error that may be included with any of the calculations. For example, the registration of the body surface to the patient model may include some level of uncertainty or error that may be propagated through the setting of the scan parameters and further though throughout the method. For instance, the start and end slice position may include a measure of uncertainty in position due to the differences between the patient model and the actual patient. The predicted absorption curve may similarly include an estimate of uncertainty based on the uncertainty in the prediction of anatomical structures. The uncertainty measure may be obtained by generating multiple output estimates by small perturbations of the input data (e.g. small geometric perturbation which are within the sensor noise range) and computing the measure and variance of the estimates. Alternatively, a deep network may be used such as a Variational deep network that models the weights as a generalized probability distribution, and the weights are sampled from the Gaussian during the inference process. Multiple estimates are obtained by running the inference multiple times, and mean and variance of the output is obtained. Scan parameters may have an allowable range. When estimating and adjusting with the uncertainty measures, values for the scan parameters may end up outside of the allowable range. This may indicate that the system cannot accurately estimate or adjust the scan parameters and thus the scan should be halted.

At act A140, the scan is initialized using the scan parameters. If an uncertainty measure is included, the scan may use mean values and predicted values. At act A150, the scan parameters are adjusted. Adjustment of scan parameters may use machine training including comparing the predicted scan parameters with current measurements from a real time CT scan and adjusting the scan parameters based on the comparisons. The adjustments to the scan parameters may include changes to the end slice position, detector configuration, tube current, tube potential, reconstruction algorithm, patient positioning, scan range, reconstructed slice thickness, pitch, or other parameters as a function of raw CT data that is acquired during then CT scan. CT is based on the principle that the density of the tissue passed by the x-ray beam can be measured from the calculation of the attenuation coefficient. Using this principle, CT allows the reconstruction of the density of the body, by two-dimensional section perpendicular to the axis of the acquisition system. The emitter of x-rays rotates around the patient and the detector, placed in a diametrically opposite side, picks up the image of a body section (beam and detector move in synchrony). The detectors of the CT scanner 110 do not produce an image but rather measure the transmission of a thin beam (1-10 mm) of x-rays through a full scan of the body. The image of that section is taken from different angles, and this allows tomography to retrieve the information on the depth (in the third dimension). In order to obtain tomographic images of the patient from the data in "raw" scan, the computer uses complex mathematical algorithms for image reconstruction. This raw data may be used to adjust the scan parameters without requiring the complex mathematical algorithms.

The inherent differences in density in some structures may be used to discern the structures from other types of tissues or material. For example, air in the bowel lumen or the thin sleeve of fat surrounding the psoas muscles will provide different raw data, allowing the system to delineate the structures from the soft tissue shadows surrounding them without a full image reconstruction. The system may only need to identify that certain densities (e.g. raw data values) have changed by a threshold amount during the scan. Most of the abdominal organs and structures are of soft tissue (water) density, and so the images of contiguous structures merge with each other. The raw data may be used to quickly identify breakpoints or changes between such densities. This data may then be compared to the expected breakpoints or thresholds. For instance, during a thorax scan, a sharp unexpected increase in the absorption near the lower thorax region may suggest the lower edge of lungs/diaphragm and may be used to stop the full CT scan.

Figure 3:
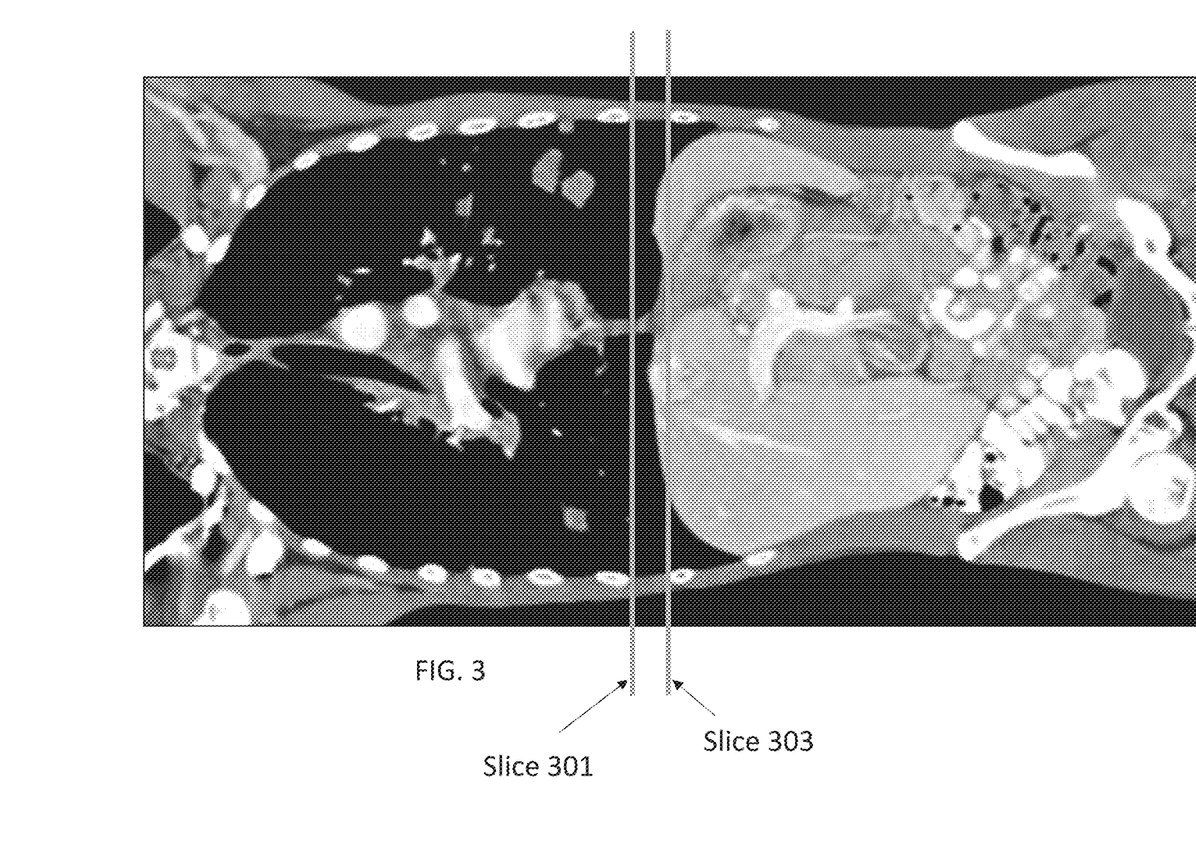
FIG. 3 depicts an example of a CT image.

FIG. 3 depicts an example CT image. In the CT image, different tissues are depicted with different greyscales. As can be seen in FIG. 3, there are distinct breaks between certain areas, for example at the lower thorax region where the anatomy transitions between the lungs and other organs. CT data is acquired in slices as the scanner moves (or patient moves). In FIG. 3, if the scanner started at the left (neck of the body) and acquired slices from through the lungs to the lower thorax region, the raw data would indicate a sharp increase in absorption between, for example, slice 301 and slice 303. The changes may result in the CT scanner 110 adjusting the start and end slice positions, detector configuration, tube current, tube potential, reconstruction algorithm, patient positioning, scan range, reconstructed slice thickness, pitch, or other parameters.

If uncertainty measures are used, the updates may be performed within the estimate of uncertainty. If the uncertainty estimates of the scan parameters are too high, then the patient should not be scanned using the proposed workflow. In an example, a patient may have an oddly shaped body, in which case the location of the internal organs is difficult to estimate. If the surface data cannot be fit to a patient model without too large an error margin, the scan parameters may be far off and may indicate that a manual scanning may be required, or a scout scan performed.

The scan parameters may be adjusted multiple times during a scan. The adjustments may continue until the scan has finished. The output of the scan is CT data that may be stored for later use or converted into a readable format for an operator or physician to review.

At act A160, a radiology report is generated from the scan data. The radiology report may be generated using a model that uses expert system rules and/or machine trained models to generate a set of findings. As an example, the findings may cover hemorrhage, bleeding, calcifications in the coronaries, organ abnormalities, among others. The model is trained on prior scan data and prior ground truth findings. After being trained using a set of training data, the model is used to generate findings in real time from scan data. The findings may then be summarized into a radiology report using natural language processing tools. Natural language processing uses one or more classifications that are generated using image processing of a radiology image from the scan. The one or more classifications are analyzed using a computer implemented text analysis process to generate a natural language sentence representing the radiology image. The image processing may include Artificial Intelligence (AI)-based image processing. For example, the radiology image may be a Coronary CT Angiography. A Recurrent Neural Network (RNN) Long Short-Term Memory (LSTM) based plaque detection AI algorithm may be applied to Coronary CT Angiography images to detect plaques. The output of this algorithm may be a classification result, which may be a multi-class label e.g., for plaque type classification (e.g., calcified, non-calcified, mixed), and/or a continuous value, e.g., for stenosis grading regression. Different networks may be used for different scan protocols or classifications.

The radiology report may include detection and highlighting of anomalies, cinematic rendering, enhanced clinical imaging, etc. The radiology report may include all volumetric analyses included with deviations from the normative database marked or highlighted. The radiology report may be provided to an operator or physician or transferred to PACS for later use. The radiology reports may be validated by radiologists before being archived and used for subsequent decision making and training data for the machine trained model. In an embodiment, the radiology report may be generated from an annotation table of various clinically relevant findings, and the annotation table may be populated using systems that parse the generated CT scans and use machine training to process the regions of the interest to detect any pathologies.

The data acquired or generated during the method of FIG. 1 may be stored and used as feedback in the various machine trained networks/models. For example, the output of the processes, (the fit model, scan parameters, radiology report) may be graded or scored by operators on their accuracy or usefulness. The scores and feedback may be used to further train the models.

Figure 4:
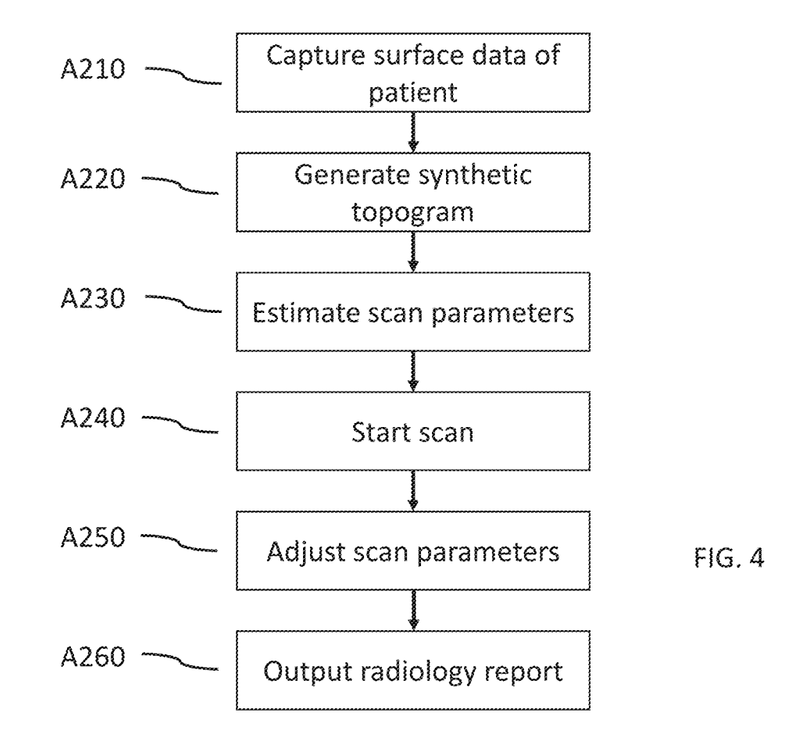
FIG. 4 depicts a flow chart diagram of one embodiment of a method for reduced interaction scanning.

FIG. 4 depicts another method for automated medical imaging. The method of FIG. 4 is performed by a medical system 100, such as the medical system 100 of FIG. 6. The method is performed in the order shown (e.g., top to bottom or numerical), but other orders may be used. Additional, different or fewer acts may be provided. The method of FIG. 4 is performed without requiring a preliminary or scout image or film of the patient. The scout scan may also be typically used as input for dose modulation software. The proposed workflow obviates the need for a scout scan by generating a synthetic topogram which is used as an input for dose modulation software and thus results in a significant boost in efficiency.

At act A210, a camera 108 captures surface data representing an outer surface of a patient. The camera 108 is directed at the patient. The camera may capture two-dimensional data or three-dimensional data. The camera 108 captures the outer surface of the patient from one or more perspectives. Any portion of the outer surface may be captured, such as the entire patient viewed from one side from head to toe and hand to hand or just the torso. The camera 108 captures the outer surface with the patient in a particular position, such as capturing a front facing surface as the patient lies in a bed or on a table for treatment or imaging.

In an embodiment, a patient model may be fit to the surface data. The patient model is a generic representation of surface of a human or part of a human. Different models may be used for different body types, such as a male or female model. The patient model is not specific to the patient. For example, the patient model is a statistical shape model. The patient model is not specific to any other patient or is specific to a patient meeting a norm. Any representation may be used for the model. In one embodiment, the model is formed from a mesh, such as a mesh of triangles. Other meshes may be used. Other representations of a three-dimensional surface may be used.

In an embodiment, surface data may include an uncertainty measure. The registration of the body surface to the patient model may include some level of uncertainty that may be propagated through the setting of the scan parameters and further though throughout the method. For instance, start and end slice positions may include a measure of uncertainty in position due to the differences between the patient model and the actual patient. A predicted absorption curve may similarly include an estimate of uncertainty based on the uncertainty in the prediction of anatomical structures. The uncertainty measure may be obtained by generating multiple output estimates by small perturbations of the input data (e.g. small geometric perturbation which are within a sensor noise range) and computing the measure and variance of the estimates. Alternatively, a deep network may be used such as a variational deep network that models the weights as a generalized probability distribution. The weights are sampled during an inference process. Multiple estimates may be obtained by running an inference process multiple times to obtain mean and variance values.

At act A220, a synthetic topogram is generated from the surface data. A scout image may not only conventionally used for region of interest specification but also may be used by dose modulation software. To expedite the workflow, a scout image is not acquired, instead, the workflow uses a synthetic topogram that approximates the true internal anatomy of the patient and is used as an input for components such as the dose modulation software.

Dose modulation software uses a scout image as input. Since there is not a scout image, the synthetic topogram is used. The synthetic topogram is generated from the surface data acquired by the sensor that is fit to the patient model. The synthetic topogram, e.g. a two-dimensional projection of the internal anatomy of a patient, is predicted from geometric measurements on the patient's body surface using deep machine training models. For example, a generative adversarial network (GAN) may generate a topogram representing interior organs based on the outside surface of the patient. To further adapt to specific patients, internal landmarks may be used in the topogram prediction. The synthetic topogram generated by the generator of the GAN may be altered based on landmarks generated by another generator.

The machine trained network is an image-to-image network, such as a generative adversarial network, trained to convert surface data to a topogram. For example, the trained convolution units, weights, links, and/or other characteristics of the network are applied to the surface data and/or derived feature values to extract the corresponding features through a plurality of layers and output the topogram. The features of the input images (e.g., surface data) are extracted from the images. Other more abstract features may be extracted from those extracted features using the architecture. Depending on the number and/or arrangement of units or layers, other features are extracted from the input. For training the machine trained network, the machine training network arrangement is defined. The definition is by configuration or programming of the training. The number of layers or units, type of training, and other characteristics of the network are controlled by the programmer or user. In other embodiments, one or more aspects (e.g., number of nodes, number of layers or units, or type of training) are defined and selected by the machine during the training.

In an embodiment, the machine trained network is an image-to-image network. Any machine training architecture for outputting a spatial distribution from an input spatial distribution may be used. For example, U-Net is used. A convolutional-to-transposed-convolutional network is used. One segment of layers or units applies convolution to increase abstractness or compression. The most abstract feature values are then output to another segment. The other segment of layers or units then applies transposed convolution to decrease abstractness or compression, resulting in outputting of a topogram or indication of class membership by location.

In an embodiment, the network is a GAN that may include convolutional neural network (CNN) or deep belief nets (DBN). Other deep networks may be used. CNN learns feed-forward mapping functions while DBN learns a generative model of data. In addition, CNN uses shared weights for all local regions while DBN is a fully connected network (i.e., having different weights for all regions of an image). The training of CNN is entirely discriminative through backpropagation. DBN, on the other hand, employs the layer-wise unsupervised training (e.g., pre-training) followed by the discriminative refinement with backpropagation if necessary.

The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit.

Rather than pre-programming the features and trying to relate the features to attributes, the deep architecture is defined to learn the features at different levels of abstraction based on an input image with or without pre-processing. The features are trained to reconstruct lower level features (i.e., features at a more abstract or compressed level). For example, features for reconstructing an image are trained. For a next unit, features for reconstructing the features of the previous unit are trained, providing more abstraction. Each node of the unit represents a feature. Different units are provided for training different features.

Within a unit or layer, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape or building indication. For transposed convolution to reconstruct, the level of abstraction reverses. Each unit or layer reduces the level of abstraction or compression.

The features of the nodes are trained by the machine using any building blocks. For example, auto-encoder (AE) or restricted Boltzmann machine (RBM) approaches are used. AE transforms data linearly, and then applies a non-linear rectification, like a sigmoid function. The objective function of AE is the expected mean square error between the input image and reconstructed images using the trained features. AE may be trained using stochastic gradient descent or other approach to learn, by the machine, the features leading to the best reconstruction. The objective function of RBM is an energy function. Exact computation of the likelihood term associated with RBM is intractable. Therefore, an approximate algorithm, such as contrastive-divergence based on k-step Gibb sampling or other, is used to train the RBM to reconstruct the image from features.

Training of AE or RBM is prone to over-fitting for high-dimensional input data. Sparsity or denoising techniques (e.g., sparse denoising AE (SDAE)) are employed to constrain the freedom of parameters and force learning of interesting structures within the data. Enforcing sparsity within hidden layers (i.e., only a small number of units in hidden layers are activated at one time) may also regularize the network. In other embodiments, at least one unit is a convolution with ReLU activation or is a batch normalization with a ReLU activation followed by a convolution layer (BN+LeakyRU+convolution). Max pooling, upsampling, downsampling, and/or softmax layers or units may be used. Different units may be of the same or different type.

A machine trained network as described may be used for different acts in the method of FIGS. 1 and 4. Different networks may be configured differently and trained with different ground truth data or training data. The output of the machine trained network that is trained to generate a synthetic topogram is depicted in FIG. 4.

In addition, if uncertainty measures are calculated at act A210, the uncertainty measures may be propagated though the rest of the method including during creation of the synthetic image, when generating scan parameters, and when initializing and adjusting the scan. In an embodiment where a patient has been previously scanned, a prior scan may be used as the basis for the synthetic topogram.

Figure 5:
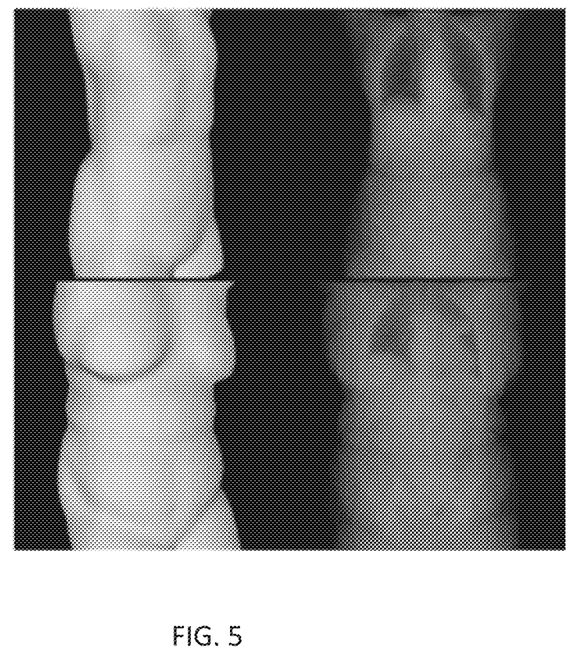
FIG. 5 depicts an example of a synthetic topogram.

FIG. 5 depicts examples of a synthetic topogram. FIG. 5 depicts two different patients (top and bottom) with fit model images on the left and synthetic topograms on the right. While the fit models only include external features, the synthetic topograms includes depict approximations of internal features of the patients. As an example, in the synthetic topograms, the location of the lungs can be distinguished.

At act A230, the synthetic topogram is input into the dose modulation software, and the dose modulation software generates scan parameters. The scan parameters may include start and end slice positions, detector configuration, tube current, tube potential, reconstruction algorithm, patient positioning, scan range, reconstructed slice thickness, pitch, among others.

Dose modulation software may be used to automatically configure the scan parameters. The dose modulation software attempts to accurately set the scan parameters so that the dose of radiation is appropriate for the scan. As an example, increases in tube current or the product of tube current and scan time (mAs) result in improved image quality, decreased image noise, but increase patient dose. The relationship between tube current and patient dose is essentially linear, with increases in mAs resulting in a comparable percentage increase in patient dose. Automated tube current modulation (also known as automated exposure control) is performed by the dose modulation software so that patient dose is kept to an appropriate level during the scan. Dose modulation software may be included with different scanners or software packages such as CARE Dose 4D on Siemens, Dose-Right on Phillips, Auto mA/Smart mA on GE, and SUREExposure three-dimensional on Toshiba among others. The dose modulation software automatically increases the mAs in those parts of the body with the greatest attenuation and decreases the mAs in those parts of the body with lower attenuation. As an example, the software increases the mAs in the shoulder and hips (that have relatively more attenuation) and decreases the mAs in the abdomen and thorax (that have relatively less attenuation).

At act A240, the scan is initialized by the CT scanner 110 with the scan parameters provided by the dose modulation software. At act A250, the scan parameters are adjusted during the scan as a function of acquired scan data during the scan. The predicted scan parameters may be compared with the current measurements as CT scan is being generated and setting the scan parameters based on the comparisons. A machine learning model may also be used that estimates or suggests scan parameters based on the current measurements. The adjustments to the scan parameters may include changes to the start and end slice positions, detector configuration, tube current, tube potential, reconstruction algorithm, patient positioning, scan range, reconstructed slice thickness, pitch, or other parameters as a function of raw CT data that is acquired during then CT scan.

In an embodiment, the dose modulation software may perform on-line attenuation-based tube current-modulation which fine-tunes the predicted optimal tube current values (estimated from the synthetic topogram data) according to the actual attenuation measured 180 degrees earlier in the tube rotation. This allows the CT scanner 110 to adapt to temporally varying levels of attenuation, such as from the injection of contrast media or due to patient motion between the acquisition of the sensor data and actual scan acquisition, as well as to optimally modulate tube current in extremely elliptical regions, such as the shoulders. A feedback system included with the dose modulation software identifies the transmission values at a given angle and uses the data to predict an optimal tube current for the projection that will occur 180 degrees later in the tube rotation. The dose modulation software lowers the tube current through areas of the body that have a decreased attenuation relative to the "reference attenuation level" of a standard-sized patient and raises the tube current where the anatomy is more attenuating.

If uncertainty measures are used, the adjustments may be performed within the estimate of uncertainty. If the uncertainty estimates of the scan parameters are too high, then the patient should not be scanned using the proposed workflow. In such a case, a manual scanning may be required.

The scan parameters may be adjusted multiple times during a scan. The adjustments may continue until the scan has finished. The output of the scan is CT data that may be stored for later use or converted into a readable format for an operator or physician to review.

At act A260, a radiology report is output after completing the scan. The radiology report may include detection and highlighting of anomalies, cinematic rendering, enhanced clinical imaging, etc. The radiology report may include all volumetric analyses included with deviations from the normative database marked or highlighted. The radiology report may be provided to an operator or physician or transferred to PACS for later use. The radiology reports may be validated by radiologists before being archived and used for subsequent decision making and training data for the machine trained models. In an embodiment, the radiology report may be generated from an annotation table of various clinically relevant findings and the annotation table may be populated using systems that parse the generated CT scans and use machine training to process the regions of the interest to detect any pathologies. All the data acquired or generated during the method of FIG. 4 may be stored and used as feedback in the various machine trained networks/models.

FIG. 6 shows one embodiment of a medical system 100 for reduced interaction medical imaging. The medical system 100 includes the display 102, memory 106, image processor 104, sensor 108, and medical scanner 110. The display 102, image processor 104, and memory 106 may be part of the medical system 100, a computer, server, workstation, or other system for diagnosis or treatment. A workstation or computer without the medical system 100 may be used with the medical system 100. Additional, different, or fewer components may be provided. For example, a computer network is included for remote processing or storage. As another example, a user input device (e.g., keyboard, buttons, sliders, dials, trackball, mouse, or other device) is provided for user alteration or setting for configuring the medical system 100.

The sensor 108 is a depth sensor or camera 108. LIDAR, 2.5D, RGBD, stereoscopic optical sensor, or other depth sensor may be used. One sensor 108 is shown, but multiple sensors may be used. A light projector may be provided. The sensor 108 may directly measure depth from the sensor 108 to the patient. The sensor 108 may include a separate processor for determining depth measurements from images, or the image processor 104 determines the depth measurements from images captured by the sensor 108. The depth may be relative to the sensor 108 and/or a bed or table 89. The sensor 108 is directed to the patient 88. The sensor 108 may be part of or connected to the medical system 100 or is separate from the medical system 100. The sensor 108 is configured to measure depths to or for a patient. The depths are distances from the sensor 108, table, or other location to the patient at various locations on the patient. Any sample pattern over the patient may be used. The sensor 108 outputs depth measurements and/or a surface image as one frame of data for an entire field of view. The sensor 108 measures over a sequence. The depths and/or images (e.g., RGBD) are measured at a given time. This may be repeated at different times, providing frames of surface data representing the patient at different times.

The image processor 104 is a control processor, general processor, digital signal processor, three-dimensional data processor, graphics processing unit, application specific integrated circuit, field programmable gate array, artificial intelligence processor, digital circuit, analog circuit, combinations thereof, or other now known or later developed device for processing surface data. The image processor 104 is a single device, a plurality of devices, or a network. For more than one device, parallel or sequential division of processing may be used. In one embodiment, the image processor 104 is a control processor or other processor of a medical therapy system 100. The image processor 104 operates pursuant to and is configured by stored instructions, hardware, and/or firmware to perform various acts described herein.

The image processor 104 is configured to fit a patient model to the surface data. A frame or multiple frames of measurements from the sensor 108 are used to fit the patient model. The frame or frames are from a different part of the sequence, such as being a frame or frames captured after the frame or frames for which occupancy is initially detected. The fitting may be an initial, partial, or coarse fitting. For example, a rigid fitting is provided before a non-rigid fitting. As another example, a coarse fitting is provided before a fine fitting. In one embodiment, the image processor 104 determines landmark locations of the patient from the measurements. Any number of landmarks may be detected and located. The image processor 104 may be configured to perform further fitting using other parts of the sequence of captured measurements. For example, the patient 88 moves after the patient model is fit. The image processor 104 refits using current frames.

The image processor 104 may be configured to form a mesh for the patient using the depths from the sensor 108. A mesh is fit to the depths or other output of the sensor as a patient model. The mesh may be fit by detection of the surface of the patient and/or by minimizing differences between a pre-determined mesh shape and the shape represented by the output of the sensor.

The image processor 104 is configured to estimate scan parameters. The scan parameters may include start and end slice positions, detector configuration, tube current, tube potential, reconstruction algorithm, patient positioning, scan range, reconstructed slice thickness, pitch, among others. The medical system 100 and scan parameters are configured, at least in part, based on the patient model as fit to the patient. The image processor 104 sets one or more values of programmable variables for imaging or treating the patient. The image processor 104 may directly configure the medical scanner 110.

The image processor 104 is configured to adjust scan parameters. The image processor may adjust the scan parameters using machine training including comparing the predicted scan parameters with the current measurements as a CT scan is being generated and adjusting the scan parameters based on the comparisons. The adjustments to the scan parameters may include changes to the start and end slice positions, detector configuration, tube current, tube potential, reconstruction algorithm, patient positioning, scan range, reconstructed slice thickness, pitch, or other parameters as a function of raw CT data that is acquired during then CT scan.

The image processor 104 is configured to generate a radiology report. The radiology report may be generated using a model that uses expert system rules and/or machine trained models to generate a set of findings. The radiology report may include detection and highlighting of anomalies, cinematic rendering, enhanced clinical imaging, etc. The radiology report may include all volumetric analyses included with deviations from the normative database marked or highlighted. The radiology report may be provided to an operator or physician or transferred to PACS for later use.

The display 102 is a CRT, LCD, projector, plasma, printer, tablet, smart phone or other now known or later developed display device for displaying the output. The display 102 is configured by loading an image into a buffer. The display 102 is configured to display an image of the patient from the sensor 108 or signaling.

The sensor measurements, fit shape model, surface data, machine trained model, scan parameters, and/or other information are stored in a non-transitory computer readable memory, such as the memory 106. The memory 106 is an external storage device, RAM, ROM, database, and/or a local memory (e.g., solid state drive or hard drive). The same or different non-transitory computer readable media may be used for the instructions and other data. The memory 106 may be implemented using a database management system (DBMS) and residing on a memory, such as a hard disk, RAM, or removable media. Alternatively, the memory 106 is internal to the processor 104 (e.g. cache).

The instructions for implementing the processes, methods, and/or techniques discussed herein are provided on non-transitory computer-readable storage media or memories, such as a cache, buffer, RAM, removable media, hard drive or other computer readable storage media (e.g., the memory 106). The instructions are executable by the image processor 104 or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The medical system 100 includes a diagnostic imaging scanner 110, such as CT, MR, PET, or SPECT system or a therapeutic radiation scanner, such as an x-ray or particle therapy system. The imaging scanner 110 operates pursuant to one or more settings and scanning parameters to treat or image a patient. The settings and scanning parameters control the location in the patient being scanned, the type of scan (e.g., pulse sequence), and/or radiation dose. The intensity, frequency, duration, and/or other settings are controlled, at least in part, based on the fit patient model. The patient model may be used to indicate a location on or in the patient, such as a region of interest, an organ location, and/or a center in one, two, or three dimensions. The medical system 100 is configured by setting values of variables to operate in a particular way appropriate for the particular patient as resting on the bed.

In one embodiment, the medical system 100 uses the fit patient model to control a position and/or movement of a bed. The bed is configured to be moved based on the fit of the patient model. For example, an organ or region of interest reflected in the fit patient model is used to move the bed so that the actual organ or region of interest of the patient 120 is at an iso-center of the medical system 100. Where the patient 120 then moves, the updated fit using further frames from the sensor 108 may be used to reposition the bed and corresponding organ or region of interest of the patient 120.

Once configured by the settings, the medical system 100 treats or images the patient. For therapy, the amount of radiation applied is based, at least in part, on the fit patient model as the scanning parameters of the scanner are determined based on the sensor data and not from a scout scan. For imaging, the medical system 100 is configured to scan an internal region of a patient and generate diagnostic information from the scan.

The medical scanner 110 is configured to generate diagnostic image information. The configuration uses settings for one or more parameters, such as an X-ray source voltage, table position and/or range of movement, gantry position and/or range of movement, focus, field of view, scan density, detector thresholds, transmission sequence, image processing settings, filtering settings, or image generation settings. Based on the fit patient model, one or more settings of the medical scanner 110 are automatically set. The patient 120 is imaged by the medical scanner 110 using the settings.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for reduced interaction medical imaging, the method comprising:
    capturing, with a camera, surface data representing a patient;
    registering, by a processor, the surface data to a model of the patient;
    calculating, by the processor, one or more uncertainty measures based on the registration of the surface data to the model of the patient;
    estimating, by the processor and a machine trained network configured to generate a generalized probability distribution of scan parameters, scan parameters for a CT scanner from the registered image data and the one or more uncertainty measures;
    initiating a diagnostic scan by the CT scanner with the scan parameters without performing an additional scan;
    adjusting, during the scan, the scan parameters as a function of acquired scan data during the scan and the one or more uncertainty measures; and
    outputting a radiology report after completing the scan.

2. The method of claim 1, wherein the scan parameters are estimated using a network trained using machine training.

3. The method of claim 1, wherein the scan parameters comprise at least one of a start slice position, an end slice position, an expected absorption curve, or dose.

4. The method of claim 3, wherein the start slice position and the end slice position correspond to anatomical landmarks identified on the registered surface data.

5. The method of claim 1, wherein estimating the scan parameters comprises:
    estimating, by the processor, a three-dimensional model of the patient; and
    using, by the processor, markers on the three-dimensional model and a selected protocol to estimate the scan parameters.

6. The method of claim 1, wherein the scan parameters are estimated by registering a prior CT scan of the patient to the surface data and using the prior CT scan to estimate the scan parameters.

7. The method of claim 1, wherein the adjustment of scan parameters using machine training comprises comparing the predicted scan parameters with current measurements from the CT scanner as the scan is being generated and setting the scan parameters based on the comparison.

8. The method of claim 7, wherein an end slice position of the scan parameters is adjusted as a function of current measurements indicating an unexpected change in density values in raw data from the CT scanner.

9. The method of claim 1, further comprising:
    stopping the scan when an estimate for the scan parameters with the one or more uncertainty measures are outside a range of errors.

10. The method of claim 1, wherein the radiology report is generated using a machine trained network trained to process one or more regions of interest and classify any pathologies present.

11. A system for reduced interaction CT scanning without preforming an additional scan, the system comprising:
   a sensor configured to capture surface data of a patient;
   a CT scanner configured to scan the patient using one or more scan parameters and generate CT scan data; and
   a processor configured to estimate, from the surface data of the patients and one or more uncertainty measures derived from the surface data, the one or more scan parameters using a machine trained network configured to generate a generalized probability distribution of scan parameters, initialize the CT scanner with the estimated one or more scan parameters, and adjust the one or more scan parameters during a scan of the patient by the CT scanner as a function of received CT scan data and the one or more uncertainty measures.

12. The system of claim 11, wherein the processor is further configured to automatically generate a radiology report from an output of the CT scanner.

13. The system of claim 12, wherein the system further comprises:
   a display configured to display the radiology report.

14. A method for reduced interaction medical imaging, the method comprising:
   capturing, with a three-dimensional camera, surface data representing an outer surface of a patient;
   generating, by a processor, a synthetic topogram from the surface data, wherein the synthetic topogram includes uncertainty measures calculated as a function of a range of possible error values during generation;
   generating, by dose modulation software, one or more scan parameters from the synthetic topogram without performing an additional scan using a machine trained network trained to obtain a generalized probability distribution of the scan parameters;
   initiating a scan by a CT scanner with the one or more scan parameters;
   adjusting, during the scan, the one or more scan parameters as a function of acquired scan data during the scan; and
   outputting a radiology report after completing the scan.

15. The method of claim 14, wherein adjusting the scan comprises: adjusting the scan parameters constrained by the range of error values.

16. The method of claim 14, further comprising: registering, by the processor, the surface data to a patient model as a function of a prior scan; wherein the synthetic topogram is generated from the registered surface data.

17. The method of claim 14, wherein outputting the radiology report comprises generating the radiology report using a machine trained model trained to classify one or more pathologies in a CT image.

* * * * *